(12) United States Patent
Gill et al.

(10) Patent No.: US 10,420,939 B2
(45) Date of Patent: Sep. 24, 2019

(54) NERVE STIMULATION TO PROMOTE NEUROREGENERATION

(71) Applicant: THE CLEVELAND CLINIC FOUNDATION, Cleveland, OH (US)

(72) Inventors: Bradley C. Gill, Cleveland, OH (US); Yaw A. Nyame, Cleveland, OH (US); Eric A. Klein, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 29 days.

(21) Appl. No.: 15/454,041

(22) Filed: Mar. 9, 2017

(65) Prior Publication Data

US 2017/0281945 A1   Oct. 5, 2017

Related U.S. Application Data

(60) Provisional application No. 62/316,465, filed on Mar. 31, 2016.

(51) Int. Cl.
*A61N 1/00* (2006.01)
*A61N 1/36* (2006.01)
*A61N 1/05* (2006.01)

(52) U.S. Cl.
CPC ....... *A61N 1/36103* (2013.01); *A61N 1/0502* (2013.01); *A61N 1/0551* (2013.01);
(Continued)

(58) Field of Classification Search
CPC ............ A61N 1/36103; A61N 1/0502; A61N 1/36164; A61N 1/205; A61N 1/326; A61N 1/0551; A61N 1/36107; A61N 1/36017
See application file for complete search history.

(56) References Cited

U.S. PATENT DOCUMENTS

| 4,585,005 A | 4/1986 | Lue et al. |
| 5,314,457 A | 5/1994 | Jeutter et al. |
| (Continued) | | |

FOREIGN PATENT DOCUMENTS

| EP | 0817660 A1 | 1/1998 |
| EP | 1517725 A1 | 3/2005 |
| (Continued) | | |

OTHER PUBLICATIONS

Huang, J. et al., "Electrical stimulation accelerates nerve regeneration and functional recovery in delayed peripheral nerve injury in rats." Eur J Neurosci. Dec. 2013; 38(12);3691-701.

(Continued)

*Primary Examiner* — Scott M. Getzow
(74) *Attorney, Agent, or Firm* — Tarolli, Sundheim, Covell & Tummino LLP

(57) ABSTRACT

Temporary or sub-threshold electrical stimulation to promote recovery of a damaged or injured nerve. Methods include promoting neuroregeneration of a nerve iatrogenically injured during a medical procedure performed on a target site of a patient's body. Methods include placing an electrical lead in electrical communication with the injured or damaged nerve. Methods further include temporarily stimulating the nerve and/or applying sub-threshold stimulation to the nerve to promote neuroregeneration of the nerve. The nerve can be a peripheral nerve.

18 Claims, 2 Drawing Sheets

(52) U.S. Cl.
CPC ..... *A61N 1/36017* (2013.01); *A61N 1/36107* (2013.01); *A61N 1/36164* (2013.01)

(56) References Cited

U.S. PATENT DOCUMENTS

| | | | |
|---|---|---|---|
| 5,433,735 | A | 7/1995 | Zanakis et al. |
| 6,073,048 | A | 6/2000 | Kieval et al. |
| 6,128,536 | A | 10/2000 | Whitehurst et al. |
| 6,993,390 | B2 | 1/2006 | Zappala |
| 7,596,414 | B2 | 9/2009 | Whitehurst et al. |
| 7,610,103 | B2 | 10/2009 | Whitehurst et al. |
| 8,332,029 | B2 | 12/2012 | Glukhovsky et al. |
| 8,352,026 | B2 | 1/2013 | Diubaldi |
| 2004/0267333 | A1* | 12/2004 | Kronberg ............... A61N 1/326 607/72 |
| 2005/0240229 | A1 | 10/2005 | Whitehurst et al. |
| 2005/0283202 | A1 | 12/2005 | Gellman |
| 2006/0015153 | A1* | 1/2006 | Gliner .................. A61N 1/3606 607/45 |
| 2006/0194724 | A1 | 8/2006 | Whitehurst et al. |
| 2007/0255369 | A1 | 11/2007 | Bonde et al. |
| 2008/0208280 | A1* | 8/2008 | Lindenthaler ........ A61B 5/4836 607/42 |
| 2010/0137938 | A1* | 6/2010 | Kishawi ............... A61N 1/0551 607/46 |
| 2010/0211172 | A1 | 8/2010 | Bellamkonda et al. |
| 2011/0077458 | A1 | 3/2011 | Rezai et al. |
| 2011/0152988 | A1 | 6/2011 | Whitehurst et al. |
| 2013/0013024 | A1 | 1/2013 | Levin et al. |
| 2013/0110220 | A1 | 5/2013 | Brown |
| 2018/0015288 | A1 | 1/2018 | Peters et al. |

FOREIGN PATENT DOCUMENTS

| | | |
|---|---|---|
| EP | 1968695 A2 | 12/2005 |
| EP | 1885438 A1 | 2/2008 |
| EP | 1789103 A2 | 4/2009 |
| WO | 2013106884 A1 | 7/2013 |
| WO | 2014121063 A1 | 8/2014 |

OTHER PUBLICATIONS

Rana et al., "Chronic electrical neuronal stimulation increases cardiac parasympathetic tone by eliciting neurotrophic effects." Circ Res. May 13, 2011; 108(10):1209-19.

English A.W. et al., "Electrical stimulation promotes peripheral axon regeneration by enhanced neuronal neurotrophin signaling." Dev Neurobiol. Feb. 1, 2007; 67(2);158-72.

Jiang, H.H. et al., "Effects of acute selective pudendal nerve electrical stimulation after simulated childbirth injury." Am J Physiol Renal Physiol 304: F239-F247, 2013. Nov. 14, 2012, pp. 1-10.

Qu, R. et al., "Neonatal colonic inflammation sensitizes voltage-gates Na+ channels via upregulation of cystathionine B-sythentase expression in rat primary sensory neorons." AM J Pyshiol Gastriointest Liver Physiol 304: G772-G772, 2013, pp. 1-10.

"A Pilot Study of the Feasibility of Chronic Cavernous Nerve Stimulation to Promote Regeneration and Erectile Function" U.S. National Library of Medicine, ClinicalTrials.gov, accessed Dec. 3, 2018, https://clinicaltrials.gov/ct2/show/NCT02006927.

* cited by examiner

100

```
┌─────────────────────────────┐
│  Placing an electrical lead in │
│ electrical communication with an│
│   injured or damaged nerve   │
│                              │
│             102              │
└─────────────────────────────┘
              │
              ▼
┌─────────────────────────────┐
│ Delivering an electrical signal to│
│   the nerve for a period of time │
│ between at least a portion of one│
│   day to six weeks to promote    │
│  neurogeneration of the nerve    │
│                              │
│             104              │
└─────────────────────────────┘
```

FIG. 1

NERVE STIMULATION TO PROMOTE NEUROREGENERATION

RELATED APPLICATION

This application claims priority from U.S. Provisional Patent Application Ser. No. 62/316,465, filed Mar. 31, 2016, the subject matter of which is incorporated hereby incorporated by reference in its entirety.

TECHNICAL FIELD

The present invention relates to using temporary or sub-threshold electrical stimulation to promote neuroregeneration of a nerve.

BACKGROUND

Neurostimulation is used in multiple areas of the body to restore or modulate normal nerve function. Intra-operative nerve stimulation has led to the development of products focused on identifying and stimulating a nerve for diagnostic and/or surgical planning purposes.

Peripheral nerve regeneration is the regrowth or repair of neural tissue, cells, or cellular components of the peripheral nervous system. Recent estimates indicate that thousands of Americans suffer peripheral nerve injuries or damage every year, including iatrogenic nerve injury. These injuries vary in severity and include inflammation, compression, transection, ischemia, degeneration, and radiation-induced damage. Peripheral nerve injuries may result in discomfort, pain, or dysfunction in corresponding parts of the body.

For example, many males who undergo prostate surgery suffer injuries to the cavernous nerve during the course of the operation. The cavernous nerve is essential in achieving and maintaining a penile erection. Thus, erectile dysfunction is a common complication for tens of thousands of males who undergo prostate surgery annually.

There have been prior attempts at achieving peripheral neuroregeneration but such attempts have either been unsuccessful or unsafe. Therefore, a need exists for a method of neuroregeneration that is effective, safe, and convenient to the patient.

SUMMARY

The present invention generally relates to promoting neuroregeneration in a damaged or injured nerve. In an embodiment, a method of promoting neuroregeneration of such a nerve comprises placing an electrical lead in electrical communication with the nerve and temporarily stimulating the nerve. The nerve can be stimulated for a time period of between a portion of at least one day to six weeks. In other additional or alternative embodiments, a method of promoting neuroregeneration in a damaged or injured nerve comprises placing an electrical lead in electrical communication with such a nerve and delivering a sub-threshold electrical signal to the nerve. The sub-threshold electrical signal promotes neuroregeneration of the nerve but does not stimulate the nerve to a level that triggers the nerve's physiological effect. In certain aspects, the nerve has been iatrogenically injured during a medical procedure performed on a target site of the patient's body.

BRIEF DESCRIPTION OF THE DRAWINGS

FIG. 1 is a flow chart outlining exemplary steps of a method according to an embodiment of the present disclosure.

DETAILED DESCRIPTION

Figure 2:
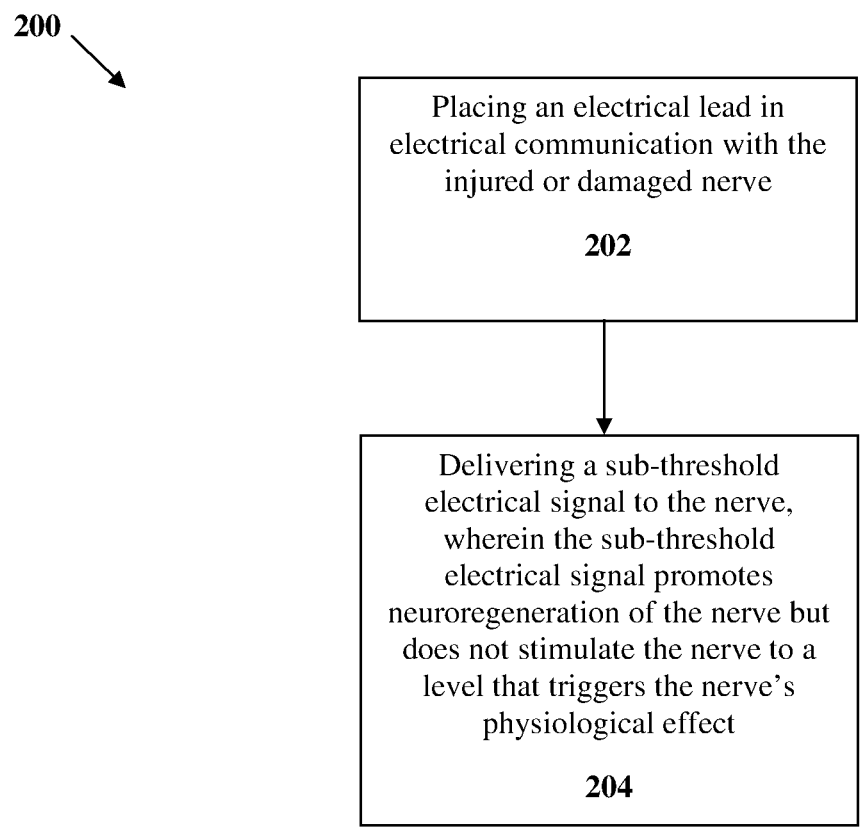
FIG. 2 is a flow chart outlining exemplary steps of a method according to an additional or alternative embodiment of the present invention.

As used herein with respect to a described element, the terms "a," "an," and "the" include at least one or more of the described element unless otherwise indicated. For example, "a nerve" includes a single nerve, a nerve trunk or a plurality of nerves such as a nerve bundle. Further, the term "or" refers to "and/or" including combinations thereof unless otherwise indicated. In addition, it will be understood that when an element is referred to as being "on," "attached" to, "connected" to, "coupled" with, "contacting," in "communication" with, etc., another element, it can be directly on, attached to, connected to, coupled with, contacting, or in communication with the other element or intervening elements may also be present. In contrast, when an element is referred to as being, for example, "directly on," "directly attached" to, "directly connected" to, "directly coupled" with, "directly contacting," or in "direct communication" with another element, there are no intervening elements present. It will also be appreciated by those of skill in the art that references to an element that is disposed "adjacent" another element may have portions that overlap or underlie the adjacent element. As used herein, a "patient" is a mammal and preferably is a human being. Although the present disclosure refers to the term electrical "stimulation," such stimulation can inhibit or activate neural activity so long as neuroregeneration is promoted.

The present disclosure generally relates to neuroregeneration of an injured or damaged nerve in a patient using localized, temporary or sub-threshold neurostimulation. In certain aspects, the present disclosure relates to using localized, temporary or sub-threshold neurostimulation for the purpose of nerve recovery or regeneration following an iatrogenic injury. Without wishing to be bound by theory, it is believed that temporary, targeted or sub-threshold electrical stimulation of damaged or injured nerves, such as those iatrogenically injured, promotes neuroregeneration by raising levels of neurotrophins and cytoskeletal proteins. Such neurotrophins are molecules that stimulate neuroregeneration. In certain aspects, methods of the present disclosure maximize nerve regeneration by placing a lead comprising an electrode in electrical communication with the damaged or injured nerve. Again, without wishing to be bound by theory, it is believed that such nerve stimulation ultimately upregulates cell activity in damaged or injured nerves and ultimately leads to improved nerve conduction, activity, and recovery of function in innervated structures. Whether neurogeneration has occurred according to systems and method described herein can be determined by a measurable increase in cytoskeletal proteins or other molecules involved in nerve regeneration and/or actual nerve functionality. Unlike other electrical stimulation methods and systems, methods and systems as disclosed herein do not serve as a mechanism for locating nerves during surgery, but instead involve a therapeutic implantable device that can remain in place for a temporary period of time and provide targeted and sub-threshold stimulation to a damaged or injured nerve.

Accordingly, referring to FIG. 1, certain aspects of the present disclosure provide a method 100 of promoting neuroregeneration of a damaged or injured nerve in a patient's body by placing an electrical lead in electrical communication with the damaged or injured nerve 102. In certain embodiments, the electrical lead is placed on or in direct electrical contact with the damaged or injured nerve. Certain aspects provide methods of promoting neuroregeneration of a nerve iatrogenically injured during a medical procedure performed on a target site of a patient's body by placing an electrical lead in electrical communication with a nerve adjacent to the target site. Such a nerve may be a nerve that is coursed during the medical procedures. Referring again to FIG. 1, in certain embodiments, an electrical signal is delivered to the nerve for a period of time between at least a portion of one day to six weeks to promote regeneration of the nerve 104. In certain embodiments, the nerve is stimulated for a period of time between one day to six weeks. In certain embodiments, the nerve is stimulated for a period of time between at least a portion of one day to 29 days. The days can be consecutive or non-consecutive.

In addition or alternatively, the nerve is stimulated with stimulation parameters that provide sub-threshold stimulation. Specifically, referring to FIG. 2, a method 200 of promoting neuroregeneration of a damaged or injured nerve in a patient's body comprises placing an electrical lead in electrical communication with the nerve 202 and delivering a sub-threshold electrical signal to the nerve 204. In certain embodiments, the electrical lead is placed on or in direct electrical contact with the damaged or injured nerve. The sub-threshold electrical signal promotes neuroregeneration of the nerve but does not stimulate the nerve to a level that triggers the nerve's physiological effect. In particular, such sub-threshold stimulation provides a regenerative effect but does not stimulate the nerve to a level that triggers the nerve's physiological effect, such as a muscle contraction (or an erection in the case of injury to the cavernous nerve).

The nerves can be peripheral nerve fibers, including but not limited to, somatic nerves (peripheral motor and sensory nerves), autonomic nerves (such as sympathetic and parasympathetic nerves), spinal nerves, and/or cranial nerves.

Exemplary medical procedures by which a nerve can be damaged include open surgical procedures, endoscopic procedures, and minimally invasive surgical procedures. Systems and methods as disclosed herein can be used to improve or prevent conditions that are associated with iatrogenic nerve injury such as erectile dysfunction associated with damage to the cavernous nerves after a prostatectomy. Other applications include treating or improving other conditions related to nerve injury where surgical dissection or visualization of a nerve occurs such as, but not limited to, recurrent laryngeal nerve injury associated with a thyroidectomy where the target site is the thyroid gland; facial nerve injury associated with a parotidectomy where the target site is the parotid gland; peripheral nerve injury associated with extremity surgery where the target site is an extremity of the patient's body; or pudendal nerve injury associated with childbirth where the target site is the birth canal.

Regarding the electrical lead, the lead can be placed in electrical communication with the damaged or injured nerve percutaneously or through open surgery. In the case of iatrogenic injury to the nerve, the electrical lead can be placed in electrical communication with the nerve before, during, or after the medical procedure. The electrical lead is placed in electrical communication with the nerve such that the electrode(s) of the electrical lead is as close to the nerve as possible without requiring further dissection that could further injure the nerve.

The electrical lead comprises an electrode or a plurality of electrodes. The electrical lead is preferably disposable and is removed from the body after up to a few weeks of use. Preferably, the lead used for the stimulation is tunneled through the subcutaneous tissues of the patient's skin and can be removed by pulling out the lead post-operatively, like a surgical drain.

Regarding particular steps of a method of the present invention, once the electrical lead is placed in electrical communication with a nerve, a controller connected to the electrical lead is activated thereby applying to the nerve an electrical signal having specified parameters. In certain embodiments, the electrical signal has an amplitude of between about 10 to about 40 mA, a frequency between about 10 to about 60 Hz, and a pulse width of between about 0.22 to about 2.0 ms. In a preferred embodiment, such stimulation parameters are used to prevent or improve a complication associated with surgery that results in erectile dysfunction. The electrical signal may be applied continuously or intermittently and the pulsing parameters, such as the pulse width, amplitude, frequency, voltage, current, intensity, and/or waveform may be adjusted to achieve the desired result of neuroregeneration. Specifically, the degree to which the nerve is stimulated to promote neuroregeneration can be controlled by adjusting these parameters. In certain embodiments, the electrical signal is an oscillating or charge-balanced signal. The waveform may be, for example, monophasic or biphasic. The waveform may be a square wave, sine wave, or other electrically safe and feasible combination including asymmetric waveforms.

The lead is connected directly or indirectly to a controller. The controller is used to operate and supply power to the electrode and enable the electrode to deliver an electrical signal to the nerve. The controller may be powered by a battery (which can be rechargeable), an external power supply, a fuel cell, or a battery pack for external use. The controller may also be integral with the lead (such as a single stimulation lead/controller). Preferably, the systems of the present invention can be powered by a portable battery-operated device. This power source allows the patient to receive therapy without impending on the patient's functional status after the medical procedure or otherwise after the nerve is treated.

The controller may change the output to the electrode by way of polarity, pulse width, amplitude, frequency, voltage, current, intensity, duration, stimulus cycling, wavelength, and/or waveform. The controller may operate any number or combination of electrodes.

The controller may be implanted within the patient or it may be positioned outside of the patient. A portion of the control system may be external to the patient's body for use by the attending physician to program the implanted controller and to monitor its performance. This external portion may include a programming wand which communicates with the implanted controller by means of telemetry via an internal antenna to transmit parameter values (as may be selectively changed from time to time by subsequent programming) selected at the programmer unit, such as a computer. The programming wand also accepts telemetry data from the controller to monitor the performance of the lead. The external wand may alternatively deliver power and the specific electrical signal to the device.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. Additionally, when describing a range, all points within that range are included in this disclosure. For example, the time period of between at least a portion of one day to 6 weeks includes all time periods within that range. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method of promoting neuroregeneration of a damaged or injured nerve in a human's body comprising:
    placing an electrical lead in electrical communication with the nerve; and
    delivering an electrical signal to the nerve for a period of time between at least a portion of one day to six weeks to promote neuroregeneration of the nerve wherein delivering an electrical signal to the nerve comprises delivering a sub-threshold electrical signal to the nerve, wherein the sub-threshold electrical signal promotes neuroregeneration of the nerve but does not stimulate the nerve to a level that triggers the nerve's physiological effect, wherein the electrical signal has an amplitude of between about 10 to 40 mA, a frequency between about 10-60 Hz, and a pulse width of between about 0.22-2.0 ms.

2. The method of claim 1, wherein the electrical signal is charge-balanced.

3. The method of claim 1, wherein the electrical signal is delivered for a plurality of days, and the plurality of days are non-consecutive.

4. The method of claim 1, wherein the nerve is iatrogenically damaged or injured during a medical procedure performed on a target site of a patient's body.

5. The method of claim 4, wherein the medical procedure involves surgical dissection or visualization of the nerve.

6. The method of claim 4, wherein the medical procedure is a prostatectomy, the target site is the prostate, and the nerve is a cavernous nerve.

7. The method of claim 4, wherein the medical procedure is a thyroidectomy, the target site is a thyroid gland, and the nerve is a laryngeal nerve.

8. The method of claim 4, wherein the medical procedure is a parotidectomy, the target site is a parotid gland, and the nerve is a facial nerve.

9. The method of claim 4, wherein the medical procedure is extremity surgery, the target site is an extremity of the patient's body, and the nerve is a peripheral nerve.

10. The method of claim 4, wherein the medical procedure is childbirth, the target site is the birth canal, and the nerve is a pudendal nerve.

11. The method of claim 4, wherein promoting neuroregeneration comprises improving a complication associated with the medical procedure.

12. The method of claim 11, wherein the complication is erectile dysfunction.

13. The method of claim 1, wherein the nerve is iatrogenically damaged or injured during a medical procedure performed on a target site of a patient's body and delivering an electrical signal comprises delivering the electrical signal to the nerve after the iatrogenic injury or damage.

14. The method of claim 1, wherein the nerve is iatrogenically damaged or injured during a medical procedure performed on a target site of a patient's body and placing the electrical lead comprises placing the electrical lead in electrical communication with the nerve before the medical procedure is performed.

15. The method of claim 1, wherein the nerve is iatrogenically damaged or injured during a medical procedure performed on a target site of a patient's body and placing the electrical lead comprises placing the electrical lead in electrical communication with the nerve while the medical procedure is performed.

16. The method of claim 1, wherein the electrode is a wire electrode.

17. The method of claim 1, further comprising chemically stimulating the nerve.

18. The method of claim 1, wherein the lead is percutaneously placed in direct electrical contact with the nerve.

* * * * *